United States Patent
Xu et al.

(10) Patent No.: US 7,557,348 B2
(45) Date of Patent: Jul. 7, 2009

(54) METHOD AND SYSTEM FOR IMAGING AN OBJECT USING MULTIPLE DISTINGUISHABLE ELECTROMAGNETIC WAVES TRANSMITTED BY A SOURCE ARRAY

(75) Inventors: Jingzhou Xu, Ann Arbor, MI (US); Xi-Cheng Zhang, Melrose, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 141 days.

(21) Appl. No.: 11/733,613

(22) Filed: Apr. 10, 2007

(65) Prior Publication Data

US 2008/0179526 A1    Jul. 31, 2008

Related U.S. Application Data

(60) Provisional application No. 60/886,666, filed on Jan. 26, 2007.

(51) Int. Cl.
*G01J 5/02* (2006.01)
(52) U.S. Cl. .................... 250/339.07; 250/339.06; 250/341.7
(58) Field of Classification Search ........... 250/339.07, 250/330, 340, 341.1, 341.8, 358.1, 341.7, 250/339.06
See application file for complete search history.

(56) References Cited

U.S. PATENT DOCUMENTS

| | | | |
|---|---|---|---|
| 5,623,145 A | 4/1997 | Nuss | 250/330 |
| 6,815,683 B2 * | 11/2004 | Federici et al. | 250/341.1 |
| 6,909,094 B2 | 6/2005 | Tran et al. | 250/341.1 |
| 6,909,095 B2 | 6/2005 | Tran et al. | 250/341.1 |
| 7,489,396 B1 * | 2/2009 | Vrhel et al. | 356/319 |
| 2004/0061055 A1 | 4/2004 | Kawase et al. | 250/330 |

OTHER PUBLICATIONS

"Terahertz imaging using an interferometric array," J. Federici, D. Gary, G. Schulkin, F. Huang, H. Altan, R. Barat, D. Zimdars, Applied Physics Letters, vol. 83, No. 12, Sep. 22, 2003, pp. 2477-2479.
"Terahertz wave reciprocal imaging," J. Xu and X.C. Zhang, Applied Physics Letters, vol. 88, No. 15, Apr. 14, 2006, pp. 1107-1109.

* cited by examiner

*Primary Examiner*—David P Porta
*Assistant Examiner*—Faye Boosalis
(74) *Attorney, Agent, or Firm*—Heslin Rothenberg Farley & Mesiti P.C.; Victor A. Cardona, Esq.

(57) ABSTRACT

A method and system for imaging an object includes transmitting distinguishable electromagnetic waves from a plurality of radiators of an antenna array, wherein each of the distinguishable electromagnetic waves is distinguishable from others by a detector. Each of the radiators transmits radiation comprising a different distinguishable electromagnetic wave. The method also includes imaging at least a portion of the antenna array onto a targeted object, wherein each image area of a plurality of image areas on the targeted object corresponds to an image of a respective radiator of the antenna array, and detecting a plurality of resultant electromagnetic waves, wherein the resultant electromagnetic waves are transmitted, scattered, or reflected by respective image areas on the targeted object in response to each of the respective image areas being illuminated by the radiation transmitted by the respective radiator of the source array.

29 Claims, 7 Drawing Sheets

METHOD AND SYSTEM FOR IMAGING AN OBJECT USING MULTIPLE DISTINGUISHABLE ELECTROMAGNETIC WAVES TRANSMITTED BY A SOURCE ARRAY

CROSS-REFERENCE TO RELATED APPLICATIONS

This application claims priority under 35 U.S.C. §1119 to U.S. Provisional Application No. 60/886,666, entitled "Method and System for Terahertz Wave Reciprocal Imaging," filed Jan. 26, 2007, which is herein incorporated by reference in its entirety.

GOVERNMENT RIGHTS STATEMENT

This invention was made with U.S. Government support under Grant No. ECS-9905881 from the National Science Foundation, Grant No. DAAD190210255 from the Army Research Office, and Grant No. NNM05AA52G from the Marshall Space Flight Center. The U.S. Government has certain rights in the invention.

BACKGROUND OF THE INVENTION

1. Technical Field

The present invention generally relates to imaging an object with electromagnetic radiation and, more particularly, to a terahertz imaging system that includes a source array and a detector that distinguishes among the electromagnetic waves transmitted by the source array.

2. Background Information

Terahertz wave imaging has generated wide interest in the past decade due to the unique advantages of terahertz radiation. Many imaging technologies in the terahertz frequency range have been developed since the first raster scanning terahertz image was reported. Terahertz wave imaging has been used in various applications, such as security sensing and quality control inspection, for example. Terahertz wave two-dimensional (2D) imaging technology has been demonstrated using pulsed terahertz waves and continuous wave (CW) terahertz radiation. In contrast to a raster scanning imaging system, a 2D imaging system dramatically reduces the time required for image acquisition. It can also support real-time terahertz wave imaging in the above applications. However, the development of 2D terahertz imaging systems has been hindered by several problems. One problem is that current 2D terahertz wave detector arrays currently suffer from low sensitivity. Another problem is that integrating some terahertz wave detectors, such as the heterodyne detector, is difficult where a large number of pixels is desired. A third problem is that dilution in the terahertz wave's intensity over the entire 2D detector array causes current 2D terahertz imaging systems to have low signal-to-noise ratios.

A typical active imaging system is presented in FIG. 1, wherein a point source is used to provide the carrier wave for imaging. The electromagnetic wave from the point source is expanded by a lens and illuminates the entire target. An imaging lens is used to project the image of the target onto a detector array, which is either a film or a charge coupled device (CCD) detector for an optical image. A well-known imaging equation, $1/d_t + 1/d_d = 1/F_i$, shows the relationship among the distances from the imaging lens to the target ($d_t$), the imaging lens to the detector array ($d_d$) and the focal length of the imaging lens ($F_i$). The magnification of the imaging system, $M = |d_d/d_t|$, gives a ratio between the dimensions of the image and the target.

However, this imaging system structure of FIG. 1 cannot be applied in an imaging system in the terahertz frequency range because there is currently no suitable 2D detector array available for the signals in the terahertz frequency band. Therefore, known methods of 2D terahertz wave imaging utilize a single detector and raster scanning of each pixel of the image across the detector.

Thus, a need exists for a two-dimensional terahertz imaging system that acquires an image of a targeted object more quickly than a raster scanning imaging system and that does not require a two-dimensional detector array.

SUMMARY OF THE INVENTION

Briefly, the present invention satisfies the need for a method and system for imaging an object with a single detector more rapidly by detecting the information for the pixels of the image concurrently.

The present invention provides, in a first aspect, a method of imaging an object that comprises transmitting distinguishable electromagnetic waves from a plurality of radiators of an antenna array, wherein each of the distinguishable electromagnetic waves is distinguishable from others of the distinguishable electromagnetic waves by a detector. Each of the radiators transmits radiation comprising a different distinguishable electromagnetic wave of the distinguishable electromagnetic waves. The method also comprises imaging at least a portion of the antenna array onto a targeted object, wherein each image area of a plurality of image areas on the targeted object corresponds to an image of a respective radiator of the radiators of the antenna array, and detecting a plurality of resultant electromagnetic waves, wherein the resultant electromagnetic waves are transmitted, scattered, or reflected by respective image areas of the plurality of image areas on the targeted object in response to each of the respective image areas being illuminated by the radiation transmitted by the respective radiator.

In another aspect, the present invention provides a system for imaging an object. The system comprises a source array for transmitting distinguishable electromagnetic waves from a plurality of radiators of the source array, wherein each of the radiators transmits radiation comprising a different distinguishable electromagnetic wave of the distinguishable electromagnetic waves. The system also includes a source imager for imaging at least a portion of the source array onto a targeted object, wherein each image area of a plurality of image areas on the targeted object corresponds to an image of a respective radiator of the radiators of the source array. The system further comprises a detector for detecting a composite resultant electromagnetic wave, which comprises a plurality of resultant electromagnetic waves, the resultant electromagnetic waves being transmitted, scattered, or reflected by respective image areas of the plurality of image areas on the targeted object in response to each of the respective image areas being illuminated by the radiation transmitted by the respective radiator. Each of the distinguishable electromagnetic waves is distinguishable from others of the distinguishable electromagnetic waves by the detector.

These, and other objects, features and advantages of this invention will become apparent from the following detailed description of the various aspects of the invention taken in conjunction with the accompanying drawings.

DETAILED DESCRIPTION OF THE INVENTION

The present invention provides, in one aspect, a method of and system for imaging an object, wherein distinguishable electromagnetic waves are transmitted from a plurality of radiators of a source array, such as an antenna array. Each of the radiators transmits radiation comprising a different distinguishable electromagnetic wave of the set of distinguishable electromagnetic waves transmitted by the source array, and each of the distinguishable electromagnetic waves transmitted by the source array is distinguishable from the other distinguishable electromagnetic waves by a detector. At least a portion of the source array is imaged onto a targeted object, wherein each image area of a plurality of image areas on the targeted object corresponds to an image of a respective radiator of the source array. In response to being illuminated by the radiation transmitted by a corresponding radiator of the source array, each respective image area of the targeted object may transmit, scatter, or reflect the incident radiation to produce a resultant electromagnetic wave. In one embodiment, in accordance with an aspect of the present invention, a single detector detects a composite resultant electromagnetic wave, which comprises a plurality of resultant electromagnetic waves produced by a plurality of respective image areas on the targeted object. The detector distinguishes each of the plurality of resultant electromagnetic waves of the composite resultant electromagnetic wave.

In accordance with an aspect of the present invention, a reciprocal imaging method utilizes an encoding/decoding image readout technique that allows a single detector to produce a two-dimensional (2D) image with parallel processing. Applying this technique to pulsed terahertz imaging, applicants have demonstrated that it is possible to obtain 2D terahertz images with one hundred pixels per frame, while obtaining the same signal-to-noise ratio (SNR) as a raster scanning image and providing an increase in data acquisition speed of approximately two orders of magnitude. By utilizing a method in accordance with an aspect of the present invention, a single laser oscillator may by used to create a two-dimensional, pulsed terahertz image.

Figure 1:
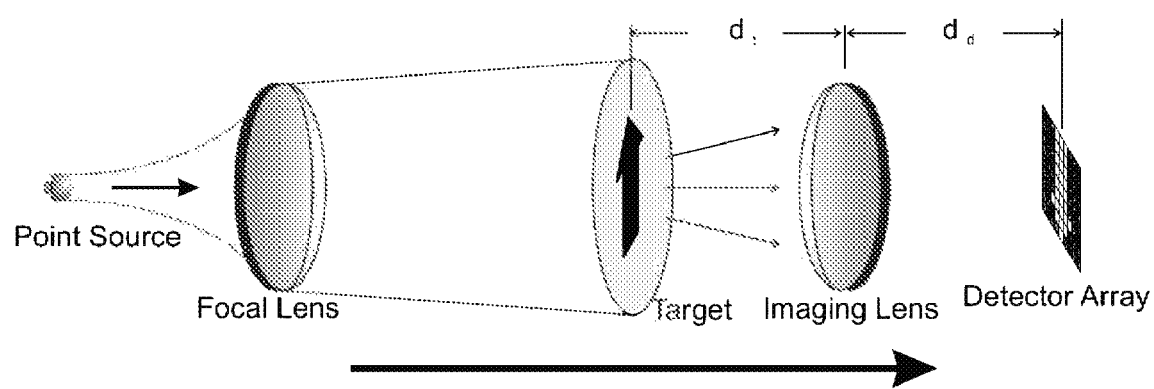
FIG. 1 illustrates a typical active imaging system comprising a point source of electromagnetic radiation and a two-dimensional detector array.
Figure 2:
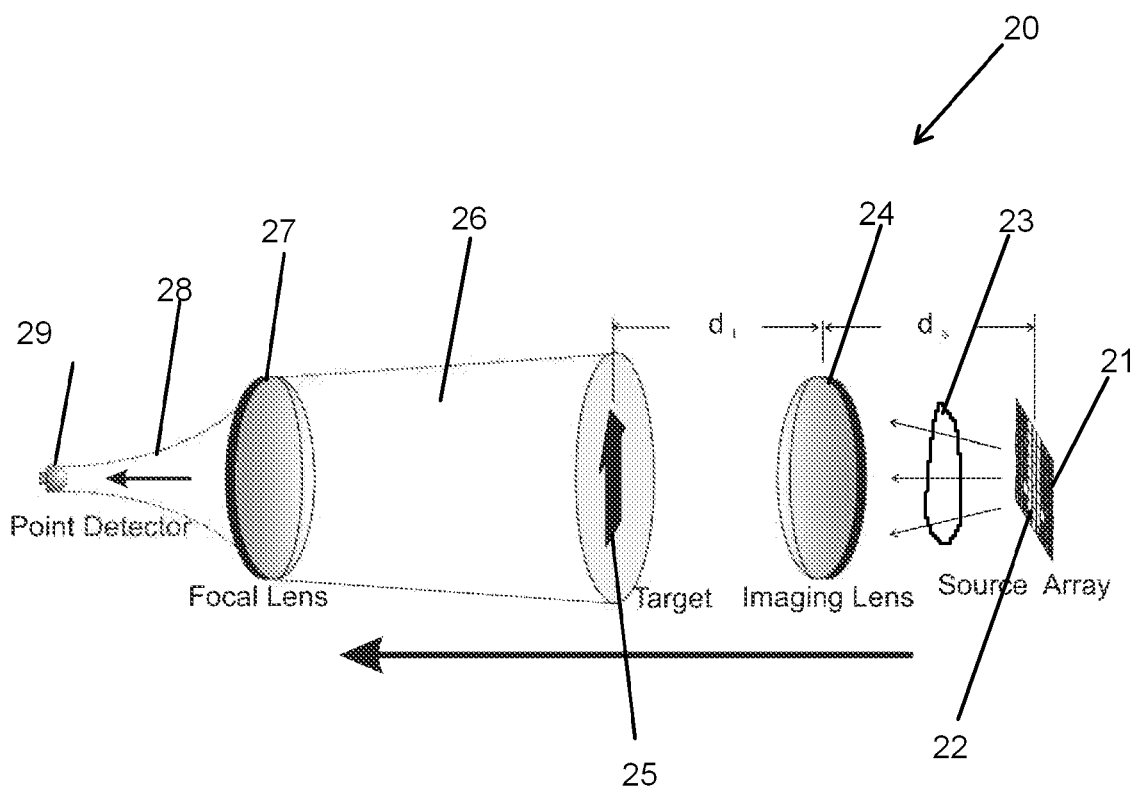
FIG. 2 illustrates one embodiment of a system for imaging an object in accordance with an aspect of the present invention.

FIG. 2 illustrates one embodiment of a system for imaging an object in accordance with an aspect of the present invention. Applicants also refer herein to a system for imaging an object, such as the system illustrated in FIG. 2, as a reciprocal imaging system because it operates in a manner that is the opposite of a traditional imaging system of the type illustrated in FIG. 1. Referring to FIG. 2, imaging system 20 comprises source array 21, source imager apparatus 24, focal apparatus 27, and detector 29. Source array 21 comprises multiple radiators 22, each of which transmits an electromagnetic wave that is distinguishable from the electromagnetic waves transmitted by the other radiators of the source array by the detector. Source imager 24 images at least a portion of source array 21 onto targeted object 25 and focuses electromagnetic radiation 23 from source array 21 on a plane that intersects the targeted object. As a result, each of a plurality of image areas, or pixels, on the targeted object corresponds to an image of a respective radiator 22 of the source array, and each image area (pixel) of the targeted object is illuminated by the radiation transmitted by the corresponding radiator. The radiators of the source array that are imaged onto targeted object 25 are shown as unshaded in the example of FIG. 2. Also, in the example illustrated in FIG. 2, targeted object 25 transmits a plurality of resultant electromagnetic waves 26, wherein an image area transmits a resultant electromagnetic wave of the plurality of resultant electromagnetic waves 26 in response to being illuminated by the radiation transmitted by the corresponding radiator of the source array. Focal apparatus 27 focuses resultant electromagnetic waves 26 on detector 29 as composite resultant electromagnetic wave 28.

Detector 29 may be coupled to a signal processor for distinguishing the distinct resultant electromagnetic waves included in the detected composite resultant electromagnetic wave or for determining the signal strengths of the plurality of resultant electromagnetic waves detected. Since the signal comprising the response of each of a plurality of image areas of the targeted object to incident radiation from the source array can be distinguished by the signal processor, an image of the targeted object may be generated. For example, in one embodiment, the signal processor estimates the signal strengths for the plurality of resultant electromagnetic waves detected and generates image information representing a two-dimensional image of the targeted object from a spatial map of the signal strengths. Because there is a correspondence between a distinguishable electromagnetic wave and the location of the source array's radiator that transmits the distinguishable electromagnetic wave, and because at least a portion of the source array is imaged onto the targeted object, the signal processor may be provided with information that facilitates assignment of the signal strength information for a resultant electromagnetic wave to an appropriate location in a spatial map that represents the image areas in a plane located at the targeted object.

As will be appreciated by those of ordinary skill in the art, the source imager 24 for imaging at least a portion of the source array onto a targeted object may comprise a lens, lens system, a pin-hole imaging device, a mirror, or a mirror set, for example. Also, focal apparatus 27 of FIG. 2 may comprise a focal lens or a concave mirror, for example.

In one embodiment, a small-gap photoconductive (PC) dipole antenna is used as the source of terahertz pulses. The small-gap photoconductive dipole antenna utilizes approximately 10 mW of excitation power and a bias voltage of approximately 10 V. Applicants have found that this radiator provides intense terahertz pulses and that the detection SNR is above $10^5/Hz^{1/2}$. A femtosecond laser oscillator with 1 W average power has the capability to excite 100 PC antennas without degrading their performance. Using current integrated circuit and optics technology, it is feasible to fabricate a PC antenna array with multiple pixels having a pixel size of approximately 1 mm or so. A polyethylene lens may be used to image the source array onto the target. Advantageously, image quality may be maintained by balancing the paraxial condition in the imaging system. In one embodiment, a lens with a shorter focal length is used to feed the terahertz pulses into a terahertz detector, which is either another PC antenna or an electro-optical (EO) crystal. A wide-angle-lens, such as a hyper-spherical silicon lens, is used to collect the terahertz pulse from a wide angle. The electric field of terahertz pulses may be measured by the detector by gating the detector with optical pulses from the same laser that excites the source antenna array.

The following analysis further illustrates the operation of one embodiment of an imaging system, in accordance with the present invention, where the targeted object only transmits incident radiation from the source array. Let the amplitude of the terahertz field at each pixel (i.e., radiator) of the source array be denoted $E_{ij}$, where i and j are the matrix indices of the 2D source array. If the targeted object only transmits the incident radiation from the source array with a spatially-dependent transmission factor, the response of each image area of the targeted object to the incident radiation may be characterized by an image-area transmission factor $T_{ij}$ because of the imaging of the source array onto the targeted object. Consequently, the spatial distribution of the electric field after the targeted object is $E''_{ij}=M^{-1}E_{ij}T_{ij}$, where M is the magnification of the source imager. The detected signal in the single detector for the composite resultant electromagnetic wave is:

$$S = \sum_{i,j} M'^{-1}M^{-1}E_{ij}T_{ij} \equiv \sum_{i,j} S_{ij}, \quad (1)$$

where M' is the magnification from the targeted object to the detector. If M and M' are equal to 1, then $S_{ij}=E_{ij}T_{ij}$, which means that each component in the detected signal represents the electric field from one radiator multiplied by the transmission factor of one spot (i.e., image area) on the target. If the electromagnetic wave transmitted by each radiator of the source array is distinguishable, the signal $S_{ij}$ for the detected response of each image area may be determined, and the spatial distribution the response of the targeted object may be mapped.

From the above, it is apparent that each component $S_{ij}$ of the detected signal for composite resultant electromagnetic wave is proportional to the full power of one radiator of the source array; therefore, the SNR of the 2D image is the same as a single spot terahertz time domain spectroscopy measurement. Because the electric field of the terahertz pulse transmitted by a radiator is proportional to the excitation intensity, if the same excitation power is used to excite ten thousand radiators in the source array, the terahertz electric field from each radiator is reduced by a factor of 100. However, the SNR for an image obtained using such a source array may be as large as 1000 without considering the collection losses of lenses in the system. For example, a source imager lens may have a collection loss due to the paraxial condition, but this is a common loss in any 2D imaging system. Advantageously, this analysis leads to the conclusion that, in a pulsed terahertz imaging system, using the reciprocal imaging method, in accordance with an aspect of the present invention, may improve the image signal-to-noise ratio by at least two orders of magnitude in comparison to a traditional imaging method under similar conditions. On the other hand, the electric field generated from each pixel (radiator) of the source array may not have the same value. Non-uniformity in the strengths of the electromagnetic fields of the radiators of a source array may affect the uniformity of the image, but this problem may be solved by using a reference image, which is obtained from the system without a targeted object present, to compensate the image information generated by the system's signal processor when imaging a targeted object.

Embodiments of a reciprocal imaging system, in accordance with an aspect of the present invention, are not limited to pulsed terahertz imaging systems. Other embodiments include continuous wave (CW) terahertz imaging systems. A heterodyne detector in the terahertz frequency range is extremely sensitive. Such a detector has a noise equivalent power that is typically in the range from $10^{-19}$ W/Hz$^{1/2}$ to $10^{-21}$ W/Hz$^{1/2}$. However, it is great challenge to develop a heterodyne detector array (especially for a large integration density) due to the local oscillator requirement. In one example of a continuous wave terahertz imaging system, a source array comprises multiple terahertz sources. In other embodiments of a continuous wave imaging system in accordance with an aspect of the present invention, one terahertz source is split into multiple outputs, which drive the radiators of the source array. A single heterodyne detector is utilized to detect the composite resultant electromagnetic wave, which comprises the responses of illuminated image areas of the targeted object to the respective incident distinguishable CW electromagnetic waves transmitted by the radiators of the source array. Because the detector distinguishes among the radiation transmitted by the radiators of the source array, the system may perform 2D terahertz wave imaging by concurrently detecting the resultant electromagnetic waves transmitted, scattered, or reflected by the image areas. The distinguishable CW electromagnetic waves are electromagnetic waves having different fundamental frequencies, for example.

In accordance with an aspect of the present invention, there are several techniques for providing a set of electromagnetic waves that are distinguishable using a single detector. As mentioned above, each radiator of the source array transmits an electromagnetic wave having a different fundamental or carrier frequency in one embodiment. In another embodiment, each radiator transmits an electromagnetic wave comprising a different time sequence of one or more pulses. One way to read out a 2D image using a single detector is to excite the radiators of the source array one by one in a timed sequence. For example, a pulsed terahertz system with a 4000 waveforms/second readout speed supports an imaging speed of 40 frames per second with 100 pixels per frame.

An alternative image readout technique comprises encoding the electromagnetic waves transmitted by each radiator of a source array and decoding them in the detector or by data processing in a signal processor coupled to the detector. Using this technique, the system produces 2D images by concurrently detecting the resultant electromagnetic waves transmitted, scattered, or reflected by the image areas of the targeted object (i.e. pixels of the targeted object) in response to illumination by respective encoded, distinguishable electromagnetic waves, which are transmitted the source array's radiators. For instance, a direct encoding method modulates the output from each radiator of the source array with a different modulation frequency. This modulation may be applied to a pulsed terahertz source by using an alternating current (AC) voltage, having the modulation frequency, to bias the radiator's antenna, instead of using a DC voltage as the bias for antenna. In one embodiment, the composite signal received by the detector is processed in a digital signal processor (DSP) chip to distinguish or separate the signals modulated at each frequency. In one exemplary embodiment, Fourier transformation processing, such as a Discrete Fourier Transform or a Fast Fourier Transform is used to distinguish the signals transmitted, scattered, or reflected by the image areas of the targeted object. Advantageously, the virtual lock-in technology provided by Fourier transformation processing may also enhance the SNR of the detected signals in addition to distinguishing the signals from each radiator of the source array.

In one embodiment, to avoid cross-talk between image pixels, the modulation frequencies used are the following prime numbers, 2, 3, 5, 7, 11, 13, 17, 19, et cetera. In another embodiment, a set of modulation frequencies comprising a multiple of these prime numbers is used in order to speed up the data acquisition. For example, the prime numbers 2, 3, 5, 7, 11, 13, 17, 19, et cetera, multiplied by 100 Hz may be used as the modulation frequencies. With regard to this example, there are 9592 such multiples of prime numbers (×100 Hz) available from 200 Hz to 10 MHz. In Equation 1 above, the electric field from radiator ij of the source array is $E_{ij}$ exp $(2\pi f_{ij}t)$, where $f_{ij}$ denotes the modulation frequency of this radiator. Signal $S_{ij}$ inherits the modulation frequency from the radiator, and, for the case of the incident electromagnetic wave being transmitted by the image area of the targeted object, the detected signal component from image area ij is $S_{ij}(t)=E_{ij}T_{ij}\exp(2\pi f_{ij}t)$. A Fourier transformation of the signal analyzes the frequency components of the composite detected signal.

Figure 3:
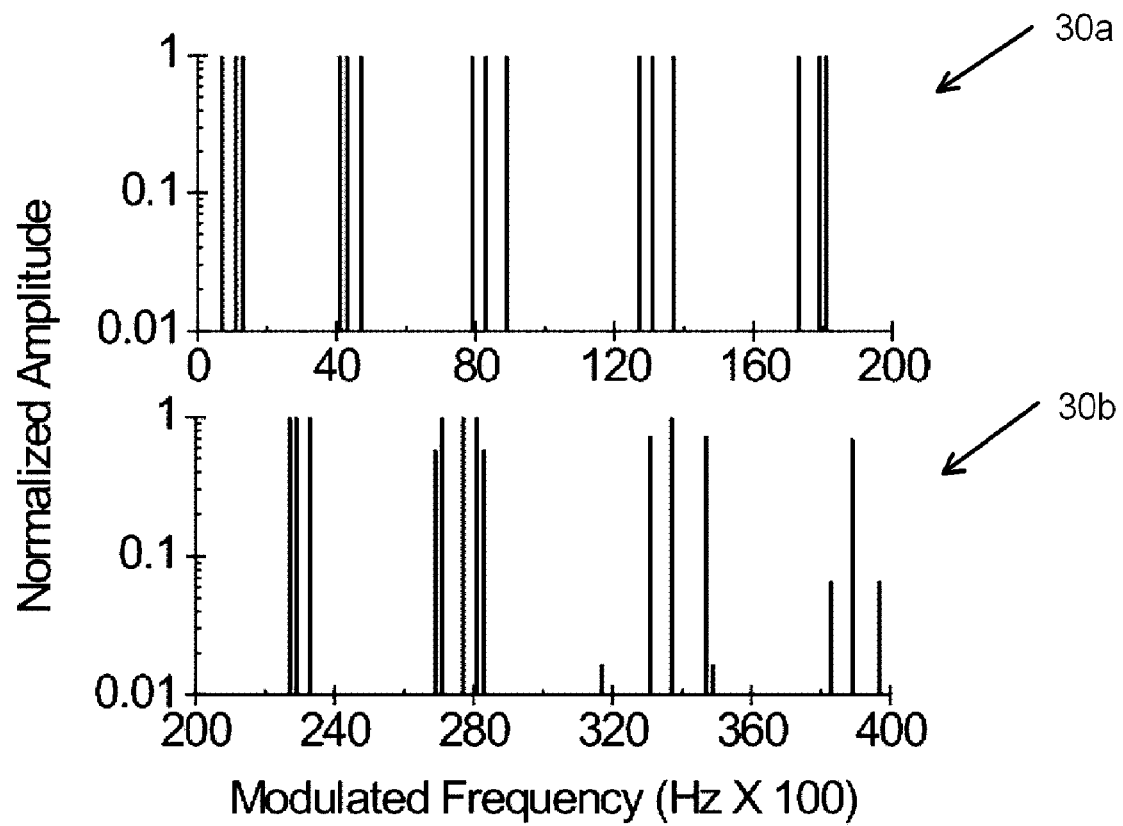
FIG. 3 illustrates the frequency spectrum of the composite detected signal for an example of the composite resultant electromagnetic wave transmitted by the targeted object in FIG. 2.
Figure 4:
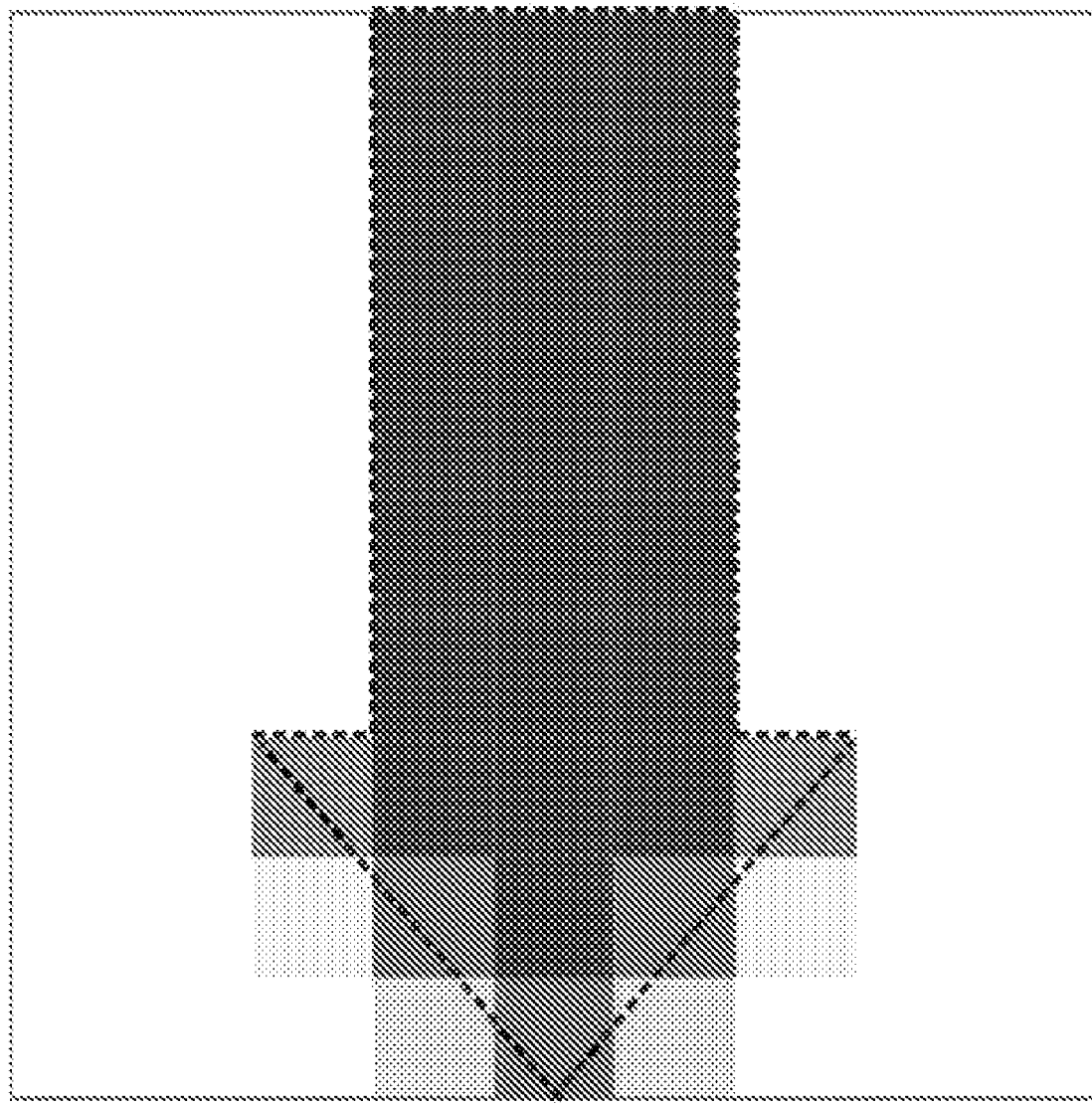
FIG. 4 illustrates an image of the arrow target in FIG. 2 generated from a spatial mapping of detected signal strengths by an imaging system, in accordance with an aspect of the present invention.

FIG. 3 illustrates the frequency spectrum of the composite detected signal for the composite resultant electromagnetic wave transmitted by the target object (comprising a transparent arrow) in FIG. 2, wherein the source array comprises a nine by nine array of radiators. The magnitude spectrum of FIG. 3 is illustrated as two plots, wherein plot 30a illustrates the magnitude spectrum of signal components having modulation frequencies from 0 to 200 Hz, and plot 30b illustrates the magnitude spectrum of signal components having modulation frequencies from 200 to 400 Hz. The value at each discrete frequency in plots 30a and 30b indicates the transmission factor of the targeted object measured using an incident electromagnetic wave that is modulated by that modulation frequency. In this example, the transmitted signal strength is proportional to the portion of the corresponding pixel (image area) that is covered by the arrow feature on the target. A spatial mapping of the magnitudes of frequency components detected generates an image of the targeted object. FIG. 4 illustrates an image of the arrow target generated by this spatial mapping.

Multiples of prime numbers are used to avoid interference between the harmonics of a modulation frequency and other modulation frequencies. Since only lower orders of the harmonic frequencies of one modulation frequency will interfere with other modulation frequencies, other frequencies that are not prime numbers may also be used as modulation frequencies. Furthermore, if the signal processor of the system is able to distinguish the phase of a signal, two sources (or two radiators of a source array) sharing the same modulation frequency, but with a 90° phase between their modulating signals, will be distinguished by the signal processor. By utilizing this feature, the number of distinguishable modulation signals doubles.

Figure 5:
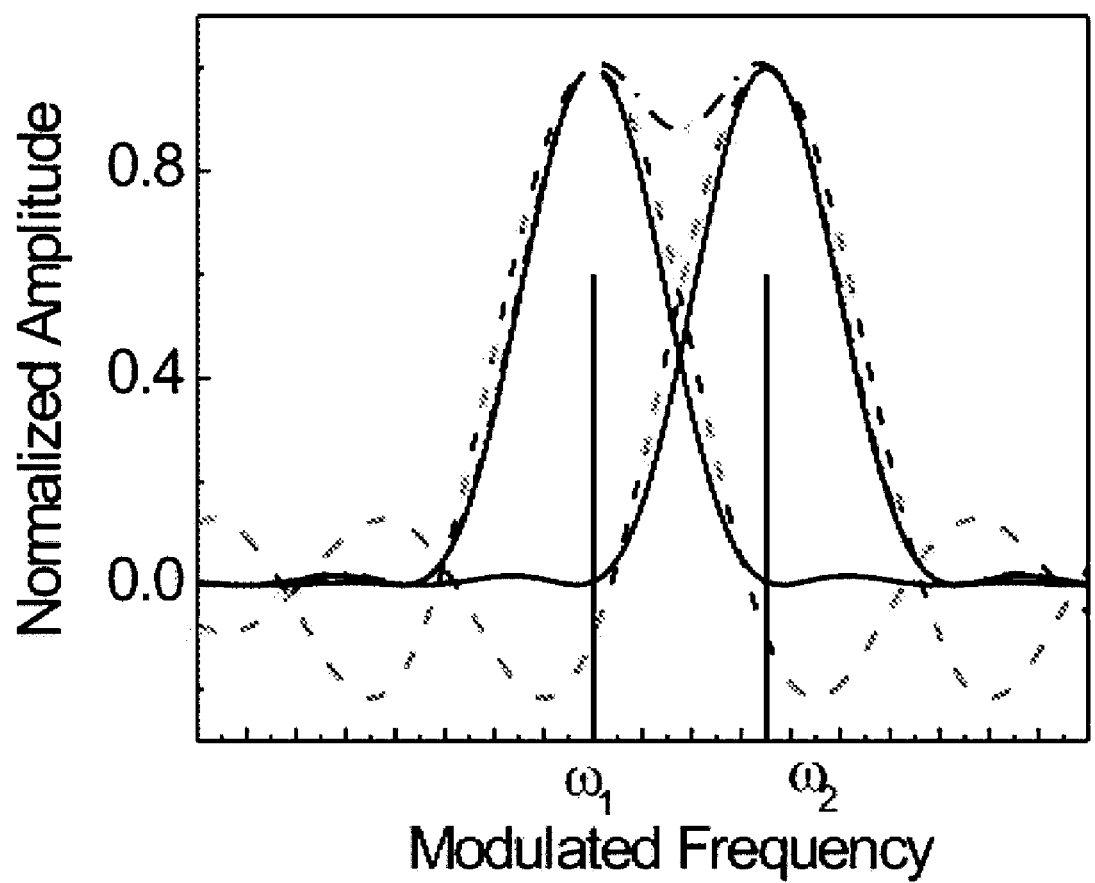
FIG. 5 illustrates a plot that compares of the diffractive limit of an imaging system in distinguishing two adjacent pixels to the bandwidth extension of the data acquisition in order to separate the two closest modulation frequencies for one embodiment in accordance with an aspect of the present invention.

In one embodiment, the parameters of the imaging system have the following relationship to utilize the source array and source imaging lens efficiently. The spatial resolution of the imaging system on the source side ($r_s$) equals the dimension of a single source (or single radiator of a source array), which is $r_s=1.22\lambda D/d_s$ where D is the diameter of the source imaging lens, and $d_s$ is the distance between the source and the source imager (e.g. imaging lens). In the encode/decode image readout process discussed above, the pixel resolution is also affected by the data acquisition time, which extends the bandwidth of the modulation frequency in detection. Source ij, provides a terahertz field of $E_{ij}$ exp $(2\pi f_{ij}t)$. If the image acquisition time is T, then the detected signal is $S_{ij}(t)=E_{ij}$ exp $(2\pi f_{ij}t)T_{ij}S(T)$, where S(T) is a square function with a period of T. The Fourier transform of the detected signal is:

$$S_{ij}=E_{ij}T_{ij}\delta(f_{ij})\sin(\pi f_{ij}/T)/(\pi f_{ij}/T), \quad (2)$$

which is a Sinc function with a main lobe width of 2/T centered at the frequency $f_{ij}$. It behaves like a wave diffracted by a slit. In a diffractive limit imaging system, a point is extended into a spot with a spatial distribution following a first Bessel function. The plot of FIG. 5 illustrates a comparison of the diffractive limit of an imaging system in distinguishing two adjacent pixels to the bandwidth extension of the data acquisition in order to separate the two closest modulation frequencies. The plot of FIG. 5 indicates that, if the space between the two closest modulation frequencies Δf is larger than bandwidth extension 2/T, the encode/decode image readout process, in accordance with an aspect of the present invention, can distinguish all of the signals for the image pixels at the same level as the spatial resolution of the imaging system in a diffractive limit condition (or better). In the set of modulation frequencies discussed above, the smallest frequency gap between two modulation frequencies, except 200 Hz and 300 Hz, is 200 Hz. As a result, the use of this set of modulation frequencies supports a data acquisition rate of 100 Hz since each of the signals transmitted by a radiator of the source array may be distinguished from the others by the detector's signal processor.

In another embodiment, a reciprocal imaging method, in accordance with an aspect of the present invention, is utilized in an interferometric imaging system. An interferometric imaging system uses a plurality of discrete distributed detectors to measure a targeted object's response to incident electromagnetic radiation. An image of the targeted object is reconstructed based on the interference between the signals detected by each pair of detectors, which forms the baseline. One advantage of interferometric imaging is that it provides high spatial resolution without using a large source imaging lens.

Figure 6:
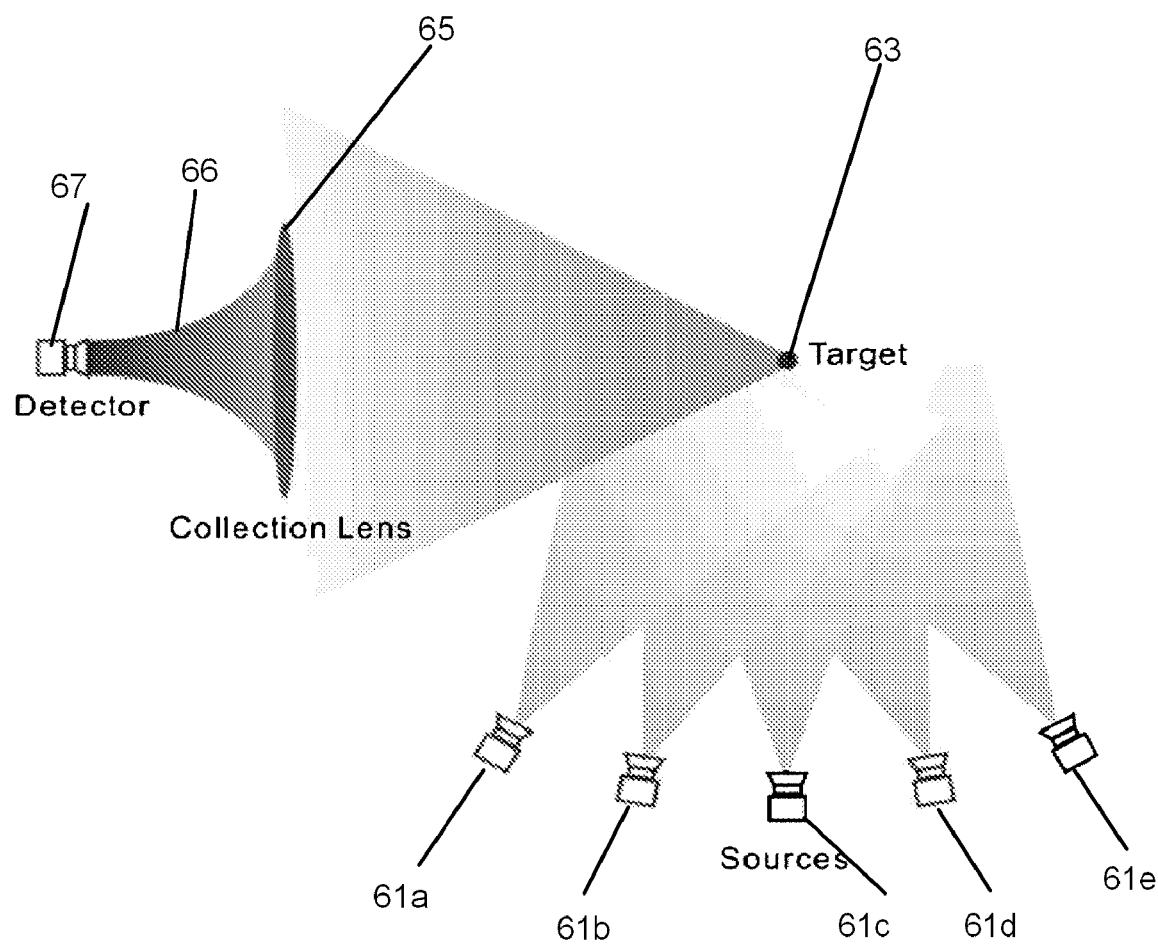
FIG. 6 illustrates an embodiment of an interferometric imaging system in accordance with an aspect of the present invention.

In one embodiment in accordance with the present invention, interferometric imaging is performed in a reciprocal way, wherein the interferometric imaging system comprises one detector 67 and multiple sources 61a-61e of distinguishable electromagnetic waves, as illustrated in FIG. 6. Multiple sources 61a-61e may be multiple radiators of a source array, such as an antenna array, for example. In the embodiment illustrated in FIG. 6, sources 61a-61e transmit a set of correlated distinguishable electromagnetic waves that illuminate targeted object 63. The targeted object may transmit, reflect, or scatter the incident electromagnetic waves. Collection lens 65 concentrates the radiation that is transmitted, reflected, or scattered in a predetermined direction by the targeted object in response to the incident electromagnetic waves. Composite resultant electromagnetic wave 66 is focused on detector 67 by collection lens 65. Targeted object 63 is resolved by the interference between each pair of sources. The distinguishable electromagnetic waves from the multiple sources may be correlated by splitting the electromagnetic radiation from one originating source into multiple outputs for the plurality of sources 61a-61e, for example. Advantageously, collection lens 65 collects the radiation that is transmitted, reflected, or scattered by the targeted object and focuses it on the detector to increase the collection efficiency of the imaging system. The efficiency of this imaging system is increased by a factor of $A_L/A_D$, where $A_L$ denotes the area of collection lens 65 and $A_D$ denotes the area of detector 67.

Modulation of the electromagnetic wave transmitted by the radiators of the source array is not the only method to encode the image. A spatially distributed modulator can be used at a source plane, target plane, or image plane to encode each pixel of the image. Also, an encoding technique, other than frequency modulation, may be used as long as the signal from each pixel can be identified in the composite signal received by the detector. The reciprocal imaging and encode/decode image readout techniques may be easily adopted for use in other frequency bands in addition to the terahertz range. The imaging method in accordance with an aspect of the present invention may be utilized advantageously in any frequency range in which a detector array is not available or not cost effective.

Figure 7:
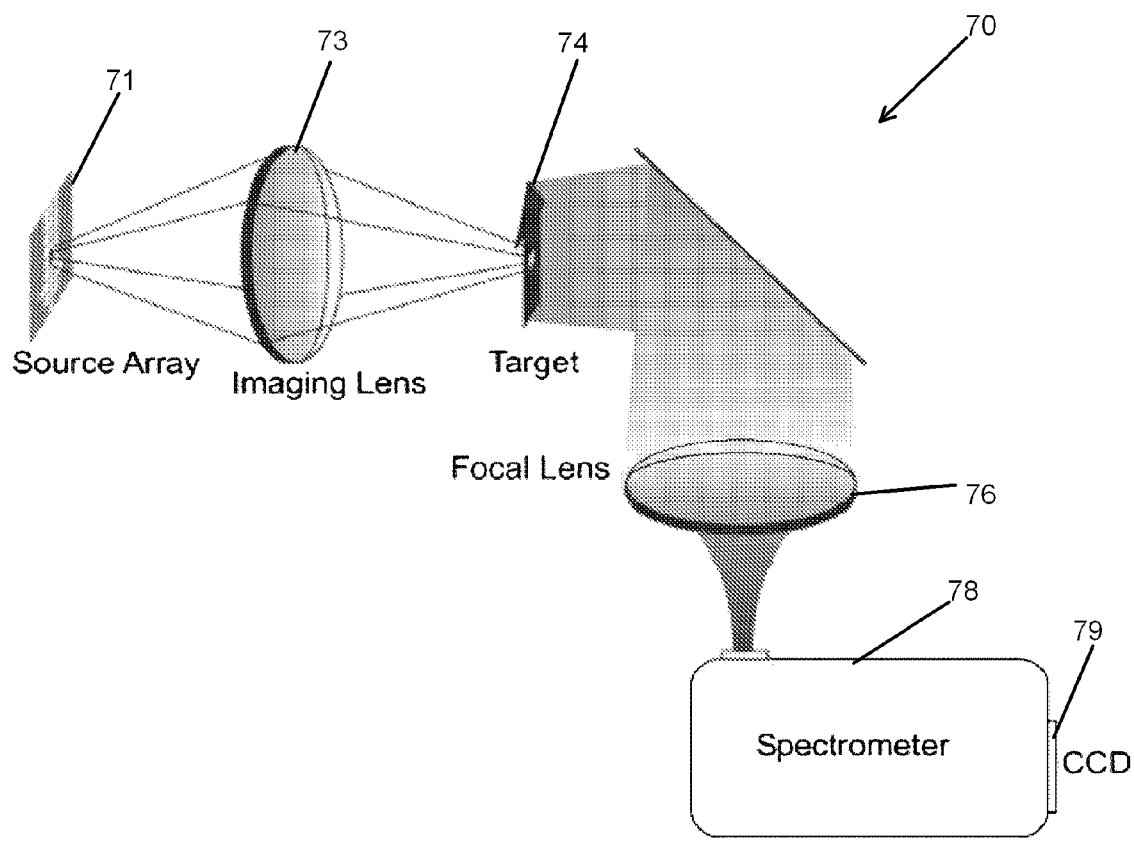
FIG. 7 illustrates a two-dimensional fluorescence imaging system that utilizes a reversed imaging method in accordance with an aspect of the present invention.

In another embodiment, FIG. 7 illustrates a two-dimensional fluorescence imaging system 70 that utilizes a reversed imaging method in accordance with an aspect of the present invention. System 70 comprises a source array 71, which transmits electromagnetic radiation, and an imaging lens 73 for imaging at least a portion of source array 71 onto a targeted object 74. The source array facilitates generation of 2D image information by transmitting a different distinguishable electromagnetic wave from each of a plurality of radiators of the source array. The source array also transmits a common electromagnetic wave from its radiators to facilitate obtaining spectroscopy information characterizing the targeted object. In addition to detecting the composite resultant electromagnetic wave and distinguishing the constituent components thereof, a method, in accordance with an aspect of the present invention, comprises receiving the targeted object's response to the incident common electromagnetic wave from the radiators of the source array using spectrometer 78. Spectrometer 78 provides a spectral analysis of the received response of the targeted object to the common electromagnetic wave, and spectrometry information provided by the spectrometer is input to charge coupled device (CCD) imager 79. In another embodiment spectrometer 78 receives a fluorescence response of the targeted object to the common electromagnetic wave, and the imaging system provides a 2D image of the targeted object together with fluorescence information characterizing the targeted object. As illustrated in FIG. 7, a focal lens 76 may be utilized to focus the response of the targeted object to the incident common electromagnetic waves on the spectrometer.

While several aspects of the present invention have been described and depicted herein, alternative aspects may be effected by those skilled in the art to accomplish the same objectives. Accordingly, it is intended by the appended claims to cover all such alternative aspects as fall within the true spirit and scope of the invention.

What is claimed is:

1. A method of imaging an object, the method comprising:
   transmitting distinguishable electromagnetic waves from a plurality of radiators of an antenna array, and wherein each of the radiators transmits radiation comprising a different distinguishable electromagnetic wave of the distinguishable electromagnetic waves;
   imaging at least a portion of the antenna array onto a targeted object, wherein each image area of a plurality of image areas on the targeted object corresponds to an image of a respective radiator of the radiators of the antenna array; and
   transmitting, scattering, or reflecting of resultant electromagnetic waves by respective image areas of the plurality of image areas on the targeted object in response to each of the respective image areas being illuminated by the radiation transmitted by the respective radiator;
   detecting by a detector a plurality of the resultant electromagnetic waves
   distinguishing each of the distinguishable electromagnetic waves from each of the others of the distinguishable electromagnetic waves to determine a location of each radiator producing each distinguishable electromagnetic wave; and
   producing an image of the targeted object based on the detection of the plurality of the resultant electromagnetic waves, the distinguishing of each of the distinguishable electromagnetic waves and the determining of the location of each radiator.

2. The method of claim 1, wherein the each of the distinguishable electromagnetic waves comprises a pulse of electromagnetic radiation.

3. The method of claim 2, wherein the electromagnetic radiation comprises a fundamental frequency in a band of frequencies from 30 gigahertz to 10 terahertz.

4. The method of claim 2, wherein a fundamental frequency and a time duration of the pulse of electromagnetic radiation facilitate distinguishing the resultant electromagnetic waves by the detector.

5. The method of claim 4, wherein the fundamental frequency is greater than or equal to two times an inverse of the time duration.

6. The method of claim 4, further comprising determining signal strengths for the plurality of resultant electromagnetic waves detected, wherein the determining utilizes a Discrete Fourier Transform or a Fast Fourier Transform of a composite detected signal, the composite detected signal comprising the plurality of resultant electromagnetic waves detected.

7. The method of claim 2, wherein pulses of the distinguishable electromagnetic waves are orthogonal in time.

8. The method of claim 1, further comprising determining signal strengths for the plurality of resultant electromagnetic waves detected.

9. The method of claim 8, further comprising generating image information representing a two-dimensional image of the targeted object from a spatial map of the signal strengths for the plurality of resultant electromagnetic waves detected.

10. The method of claim 1, wherein the detecting utilizes the detector to detect a composite resultant electromagnetic wave comprising the plurality of resultant electromagnetic waves.

11. The method of claim 10, wherein the detecting further comprises: processing the composite resultant electromagnetic wave with a spectrometer to obtain a pixel signal for each of the plurality of resultant electromagnetic waves detected; and
   measuring signal strengths of pixel signals obtained from the spectrometer for the plurality of resultant electromagnetic waves detected.

12. The method of claim 10, further comprising: distinguishing the resultant electromagnetic waves of the composite resultant electromagnetic wave; and resolving interferometric image information for the targeted object by determining interference between pairs of the distinguished resultant electromagnetic waves.

13. The method of claim 1, further comprising: transmitting a common electromagnetic wave from the plurality of radiators of the antenna array; and analyzing a response of the targeted object to the common electromagnetic wave with a spectrometer to provide spectrometry information characterizing the targeted object.

14. The method of claim 1, wherein the determining comprises corresponding each distinguishable electromagnetic wave with a location of each radiator transmitting the radiation comprising each distinguishable electromagnetic wave, and the producing the image comprising producing the image based on the corresponding.

15. The method of claim 1, wherein the detecting by the detector comprises detecting solely by a single detector.

16. The method of claim 1, wherein the distinguishing comprises distinguishing by the detector.

17. The method of claim 1, wherein the distinguishing comprises distinguishing by a signal processor.

18. A system for imaging an object, the system comprising:
a source array for transmitting distinguishable electromagnetic waves from a plurality of radiators of the source array, wherein each of the radiators transmits radiation comprising a different distinguishable electromagnetic wave of the distinguishable electromagnetic waves;
a source imager for imaging at least a portion of the source array onto a targeted object, wherein each image area of a plurality of image areas on the targeted object corresponds to an image of a respective radiator of the radiators of the source array; and
a detector for detecting a composite resultant electromagnetic wave comprising a plurality of resultant electromagnetic waves, the resultant electromagnetic waves being transmitted, scattered, or reflected by respective image areas of the plurality of image areas on the targeted object in response to each of the respective image areas being illuminated by the radiation transmitted by the respective radiator,
the detector configured to distinguish each distinguishable wave from others of the distinguishable electromagnetic waves to determine a location of each radiator producing each distinguishable wave.

19. The system of claim 18, wherein the each of the distinguishable electromagnetic waves comprises a pulse of electromagnetic radiation.

20. The system of claim 19, wherein the electromagnetic radiation comprises a fundamental frequency in a band of frequencies from 30 gigahertz to 10 terahertz.

21. The system of claim 19, wherein a fundamental frequency and a time duration of the pulse of electromagnetic radiation facilitate distinguishing the resultant electromagnetic waves by the detector.

22. The system of claim 21, wherein the fundamental frequency is greater than or equal to two times an inverse of the time duration of the pulse.

23. The system of claim 21, further comprising a signal processor for determining signal strengths for the plurality of resultant electromagnetic waves detected, wherein the signal processor computes a Discrete Fourier Transform or a Fast Fourier Transform of a composite detected signal, the composite detected signal comprising an output of the detector in response to the composite resultant electromagnetic wave detected.

24. The system of claim 19, wherein pulses of the distinguishable electromagnetic waves are orthogonal in time.

25. The system of claim 18, further comprising a signal processor for determining signal strengths for the plurality of resultant electromagnetic waves detected.

26. The system of claim 25, wherein the signal processor further comprises a two-dimensional image generator for generating image information representing a two-dimensional image of the targeted object from a spatial map of the signal strengths for the plurality of resultant electromagnetic waves detected.

27. The system of claim 26, further comprising: a spectrometer for processing the composite resultant electromagnetic wave detected by the detector; and a plurality of frequency-selective detectors for analyzing outputs of the spectrometer.

28. The system of claim 18, wherein the source imager comprises a lens, a pin-hole imaging device, or a mirror.

29. The system of claim 18, wherein the detector consists of a single detector for detecting electromagnetic waves.

* * * * *